(12) United States Patent
Kimura et al.

(10) Patent No.: US 11,931,445 B2
(45) Date of Patent: Mar. 19, 2024

(54) COMPOSITION COMPRISING BAICALIN

(71) Applicant: L'OREAL, Paris (FR)

(72) Inventors: Gisèle Kimura, Chevilly la Rue (FR); Frédérique Tabarie, Chevilly la Rue (FR); Stéphanie Cheilian, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/471,821

(22) PCT Filed: Dec. 22, 2017

(86) PCT No.: PCT/EP2017/084500
§ 371 (c)(1),
(2) Date: Jun. 20, 2019

(87) PCT Pub. No.: WO2018/115493
PCT Pub. Date: Jun. 28, 2018

(65) Prior Publication Data
US 2020/0093724 A1  Mar. 26, 2020

(30) Foreign Application Priority Data

Dec. 23, 2016 (FR) .................... 16 63316

(51) Int. Cl.
A61K 8/86 (2006.01)
A61K 8/06 (2006.01)
A61K 8/49 (2006.01)
A61K 8/81 (2006.01)
A61K 8/97 (2017.01)
A61Q 17/04 (2006.01)
A61Q 19/08 (2006.01)

(52) U.S. Cl.
CPC .............. A61K 8/498 (2013.01); A61K 8/062 (2013.01); A61K 8/8147 (2013.01); A61K 8/8152 (2013.01); A61K 8/8158 (2013.01); A61K 8/86 (2013.01); A61K 8/97 (2013.01); A61Q 17/04 (2013.01); A61Q 19/08 (2013.01)

(58) Field of Classification Search
None
See application file for complete search history.

(56) References Cited

U.S. PATENT DOCUMENTS

| 9,018,177 B2 * | 4/2015 | Lauten | A61K 8/675 |
| | | | 514/27 |
| 2013/0039963 A1 * | 2/2013 | Lorant | A61K 8/8147 |
| | | | 424/401 |
| 2014/0030297 A1 * | 1/2014 | Gaudry | A61K 8/062 |
| | | | 424/401 |
| 2014/0134120 A1 * | 5/2014 | Jouy | A61K 8/498 |
| | | | 424/59 |

FOREIGN PATENT DOCUMENTS

| CN | 102 302 504 A | | 1/2012 | |
| FR | 2 967 056 A1 | | 5/2012 | |
| FR | 2 983 071 A1 | | 5/2013 | |
| FR | 2983071 | * | 5/2013 | |
| WO | WO 2013/004777 | * | 1/2013 | ............... A61K 8/49 |
| WO | WO 2013/004777 A1 | | 1/2013 | |

* cited by examiner

Primary Examiner — Craig D Ricci
(74) Attorney, Agent, or Firm — POLSINELLI PC

(57) ABSTRACT

The invention relates to a composition in the form of an oil-in-water emulsion, in particular a cosmetic and/or dermatological composition, comprising in a physiologically acceptable aqueous medium: a) at least Baicalin and/or one of the derivatives thereof or a plant extract containing it, b) at least one superabsorbent polymer, c) at least one homo- or copolymer of non-superabsorbent acrylic acid that is at least partially neutralized, and d) at least one gemini surfactant with formula (III), said composition having a p H of 6.0 to 6.5. The invention also relates to a cosmetic care and/or makeup method for keratin materials, comprising the topical application of a composition according to the invention on keratin materials.

17 Claims, No Drawings

COMPOSITION COMPRISING BAICALIN

CROSS REFERENCE TO RELATED APPLICATIONS

This application is a National Phase filing under 35 U.S.C. § 371 of PCT/EP2017/084500 filed on 22 Dec. 2017; which application in turn claims priority to Application No. 16 63316 filed in France on 23 Dec. 2016. The entire contents of each application are hereby incorporated by reference.

The present invention relates to a composition, and in particular a cosmetic, comprising baicalin, a method for preparing such a composition, along with the uses of this composition.

Numerous cosmetic compositions comprising baicalin, or an extract containing same, as an antioxidant or photoprotector are known in prior art. Patent application EP 2729117 A1 in particular describes photoprotective compositions comprising baicalin.

However, this active constituent is very slightly soluble in an aqueous medium. It is also very sensitive to electrolytes, which makes it difficult to formulate in aqueous compositions. The solubility of baicalin increases with the pH, with the optimal pH at about 5.5. However, when the pH is more than 6.5, the active constituent is chemically unstable, thus causing its destruction.

Therefore there is a need to provide stable aqueous compositions based on baicalin.

Gel-cream type dosage forms are also frequently used, in other words oil-in-water compositions in the form of a dispersion of a fatty phase in an aqueous gel, containing little or no emulsifier. These dosage forms are appreciated for their innocuousness, but also for their sensorial effects. They have an opalescent appearance and a cool and aqueous feel during application. This type of dosage form may be obtained with superabsorbent polymers. However, large viscosity drops and phase shifts have been observed in formulations comprising these polymers. These polymers are also sensitive to electrolytes, and are difficult to formulate. Their optimal formulation pH is more than 6.5.

Therefore there is a need to provide aqueous cosmetic compositions comprising baicalin, or an extract containing baicalin, and with a cool and light feel during application. These compositions must be stable, and pleasant during application.

The aim of the invention is that of solving the technical problems cited above. In particular, one objective is to supply an aqueous composition, particularly a solvent containing baicalin, or an extract containing baicalin, and at least one superabsorbent polymer that is stable and feels cool during application.

The inventors have now discovered, surprisingly, that the addition of a specific non-superabsorbent acrylic polymer into aqueous compositions based on baicalin (or an extract containing baicalin) and a superabsorbent polymer, into an oil-in-water emulsion comprising a particular gemini surfactant can obtain stable formulas that are pleasant to apply, having a cool and light feel. Surprisingly, baicalin and the super-absorbent polymer do not degrade. No drop in viscosity nor a phase shift is observed, and baicalin does not recrystallize despite its very low solubility.

Therefore the purpose of the present is a composition in the form of an oil-in-water emulsion, in particular a cosmetic and/or dermatological composition, comprising the following in a physiologically acceptable aqueous medium:

a) at least Baicalin and/or one of the derivatives thereof or a plant extract containing it, b) at least one superabsorbent polymer, c) at least one homo- or copolymer of non-superabsorbent acrylic acid that is at least partially neutralized, and d) at least one gemini surfactant with formula (III) as described below, the composition with a pH of 6.0 to 6.5.

This invention also relates to the use, in particular cosmetic, of a composition according to the invention to reduce the pigmentation induced by UV rays.

The invention also relates to a cosmetic care and/or makeup method for keratin materials, comprising the topical application of the composition according to the invention on keratin materials.

This invention also relates to a cosmetic and/or beauty treatment method comprising the topical application of a composition according to the invention on keratin materials, particularly for combating or preventing photo-induced premature aging of keratin materials, or to protect keratin materials against solar radiation.

"Keratin materials" refers to the skin and/or lips and/or hair.

Viscosity

Compositions according to the invention preferably have a viscosity of between 45 and 70 Poises.

The viscosity measurement protocol is as follows:
The viscosity is measured with a Contraves viscosity meter equipped with the MS-r4 system with an St2 support and an MK-4 measurement body fitted with an MB-3 measurement cup. The measurements are made at a temperature of 25° C.+/−0.5° C. after 10 minutes rotation of the mobile at a speed of 200 revs/minute.

The constituents of the composition according to the invention will now be described in more detail.

Baicalin and the Derivatives Thereof

The compositions according to the invention comprise at least Baicalin or one of the derivatives thereof or a plant extract containing said compound.

Baicalin and the derivatives thereof have been described, as well as their methods of preparation, in particular in application WO2005044281. The satisfy the following general formula (I):

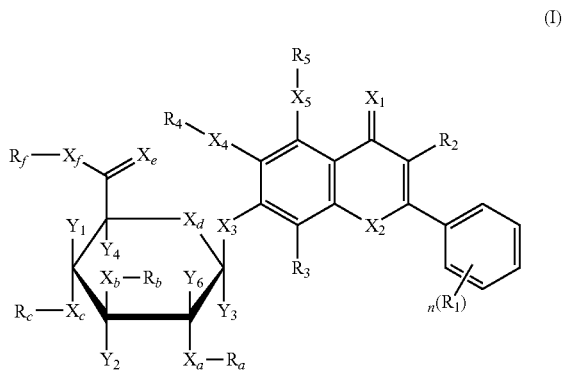

(I)

wherein

Each X1, X2, X3, X4, X5, Xa, Xb, Xc, Xd, Xe and Xf, independently, designate O or S;

Each Y1, Y2, Y3, Y4, Y6, independently, designates H or a (C1-C10)alkyl radical, in particular methyl;

Each R4, R5, Ra, Rb and Rc, independently, designates H, a (C1-C10)alkyl radial optionally substituted with 1 to 5 Ry groups, or a (C1-C10)alkyl-O—(C1-C10)alkyl radial, with each (C1-C10)alkyl radical able to be substituted with 1 to 5 Ry groups;

Each Ry, independently, designates Rq or a —(C2-C10)alkenyl, —(C2-C10)alkynyl, —(C3-C10)cycloalkyl, —(C8-C14)bicycloalkyl, —(C8-C14)tricycloalkyl, —(C5-C10)cycloalkenyl, —(C8-C14)tricycloalkenyl, phenyl, naphthyl, —(C14)aryl radical, with each one able to be substituted with one or several Rz radicals;

Each R1 R2, R3, independently, designates H or Rq or a —(C2-C10)alkenyl, —(C2-C10)alkynyl, —(C3-C10)cycloalkyl, —(C8-C14)bicycloalkyl, —(C8-C14)tricycloalkyl, —(C5-C10)cycloalkenyl, —(C8-C14)tricycloalkenyl, phenyl, naphthyl, —(C14)aryl radical, with each one able to be substituted with one or several Rz radicals;

Rf is H, (C1-C12) alkyl optionally substituted with 1 to 5 Ry radicals, (C1-C12)alkyl-O—(C1-C12)alkyl, with each (C1-C12)alkyl radical able to be substituted with 1 to 5 Ry groups;

Each Rq, independently, is CN, OH, halogen, N3, NO2, N(Rz)2, =NRz, CH=NRz, NRzOH, ORz, CORz, C(O)Rz, O(CO)ORz, SRz, S(O)Rz or S(O)2Rz;

Each Rz, independently, is —(C1-C6)alkyl, —(C2-C6)alkenyl, —(C3-C8)cycloalkyl, —(C3-C8)cycloalkenyl, phenyl, a heterocycle having 3 to 5 branches, CH(halo)2 or C(halo)3; and n is 0, 1, 2, 3, 4 or 5 as well as the salts thereof, the optical isomers thereof and/or the diastereoisomers thereof.

Certain compounds having formula (I) can have asymmetric centers and exist in various enantiomeric and diastereoisomeric forms. A compound having formula (I) can be in the form of an optical isomer or a diastereoisomer. According to the invention, compounds having formula (I) also comprise the optical isomeric forms thereof, diastereoisomers and mixtures thereof, including racemic mixtures.

The term "—(C1-C10)alkyl" means a non-cyclic saturated, linear or branched hydrocarbon chain having from 1 to 10 carbon atoms. As examples of linear saturated —(C1-C10)alkyl radicals, mention can be made of: methyl, ethyl, n-propyl, n-butyl, -n-pentyl, n-hexyl, n-heptyl, n-octyl, n-nonyl and n-decyl. As examples of branched saturated —(C1-C10)alkyl radicals, mention can be made of isopropyl, sec-butyl, isobutyl, tert-butyl, isopentyl, 2-methylbutyl, 3-methylbutyl, 2,2-dimethylbutyl, 2,3-dimethylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, -3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, -2-methyl-4-ethylhexyl, 2,2-diethylpentyl, 3,3-diehylhexyl, 2,2-diethylhexyl, 3,3-diethylhexyl.

The term "—(C2-C10)alkenyl" means a non-cyclic unsaturated, linear or branched hydrocarbon chain having from 2 to 10 carbon atoms and comprising at least one double carbon-carbon bond. As examples of —(C1-C10)alkenyl radicals, mention can be made of: 2-pentenyl 3-methyl-1-butenyl, 2-methyl-2-butenyl, 2,3-dimethyl-2-butenyl, 1-hexenyl, 2-hexenyl, -3-hexenyl, 1-heptenyl, 2-heptenyl, -3-heptenyl, 1-octenyl, -2-octenyl, 3-octenyl, 1-nonenyl, 2-nonenyl, 3-nonenyl, 1-decenyl, 2-decenyl, 3-decenyl.

The term "—(C2-C10)alkynyl" means a non-cyclic unsaturated, linear or branched hydrocarbon chain having from 2 to 10 carbon atoms and comprising at least one triple carbon-carbon bond. As examples of —(C1-C10)alkynyl radicals, mention can be made of: acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, -2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl.

The term "—(C3-C10)cycloalkyl" means a saturated hydrocarbon cycle having from 3 to 10 carbon atoms. As examples of —(C3-C10)cycloalkyl radicals, mention can be made of: cyclopropyl, cyclobutyl, cyclopentyl, cyclohexyl, cycloheptyl, cyclooctyl, cyclononyl and cyclodecyl.

The term "—(C8-C14)bicycloalkyl" means a hydrocarbon bicycle having from 8 to 14 carbon atoms and at least one saturated cycloalkyl cycle. As examples of —(C8-C14)bicycloalkyl radicals, mention can be made of: indanyl, 1,2,3,4-tetrahydronaphthyl, 5,6,7,8-tetrahydronaphthyl, perhydronaphthyl.

The term "—(C8-C14)bicycloalkyl" means a hydrocarbon tricycle having from 8 to 14 carbon atoms and at least one saturated cycloalkyl cycle. As examples of —(C8-C14)tricycloalkyl radicals, mention can be made of: pyrenyl, 1,2,3,4-tetrahydroanthracenyl, perhydroanthracenyl, aceanthrenyl, 1,2,3,4-tetrahydropenanthrenyl, 5,6,7,8-tetrahydrophenanthrenyl, perhydrophenanthrenyl The term "—(C5-C10)cycloalkenyl" means a cyclic non-aromatic hydrocarbon radical having at least one double carbon-carbon bond in the cyclic system and from 5 to 10 carbon atoms. As examples of —(C5-C10)cycloalkenyl radicals, mention can be made of: cyclopentadienyl, cyclohexenyl, cyclohexadieenyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl.

The term "—(C8-C14)bicycloalkenyl" means a hydrocarbon bicycle having at least one double carbon-carbon bond in each cycle and from 8 to 14 carbon atoms. As examples of —(C8-C14)bicycloalkenyl radicals, mention can be made of: indenyl, pentalenyl, naphthalenyl, azulenyl, heptalenyl, 1,2,7,8-tetrahydronaphthalenyl.

The term "—(C8-C14)tricycloalkenyl" means a hydrocarbon tricycle having at least one double carbon-carbon bond in each cycle and from 8 to 14 carbon atoms. As examples of —(C8-C14)tricycloalkenyl radicals, mention can be made of: anthracenyl, phenalenyl, acenaphthalenyl, as-indacenyl, s-indacenyl.

The term "—(C14)aryl" means a 14-branch aromatic carbocycle such as anthryl and phenanthryl.

The term "heterocycle having 3 to 5 branches" means a saturated, unsaturated, aromatic or non-aromatic heteromonocycle having 3 to 5 branches having carbon atoms and heteroatoms. A heterocycle with 3 or 4 branches can comprise up to 3 heteroatoms and a heterocycle with 5 branches up to 4 heteroatoms. Each heteroatom is independently chosen from a nitrogen that can be quaternized, oxygen and sulfur including sulfoxide and sulfone. The heterocycle can be attached by any heteroatom or carbon atom. As examples of heterocycles with 3-5 branches, mention can be made of: furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl.

The term "halo" means a halogen atom such as F(Fluorine), Cl (Chlorine), Br (Bromine) and I (Iodine).

The term "—CH(halo)2" means a methyl group wherein 2 of the hydrogens are replaced with a halogen atom.

Mention can be made for example of: —CHF2, —CHCl2, —CHBr2, —CHBrCl, —CHClI and —CHI2.

The term "—CH(halo)3" means a methyl group wherein 3 of the hydrogens are replaced with a halogen atom. Mention can be made for example of: —CF3, —CF2Cl, —CCl3, —CBr3, —CFBr2 and —CI3.

The term "salts of the compounds having formula (I)" means a salt formed by an inorganic or organic acid or an inorganic or organic base.

As examples of acid salts, mention can be made of sulfate, citrate, acetate, oxalate, chloride, bromide, iodide, nitrate, bisulphate, phosphate, isonicotinate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As examples of base salts, mention can be made of alkali metal hydroxides such as sodium, potassium and lithium; alkali earth-metal hydroxides such as calcium and magnesium; hydroxides of other metals, such as aluminum and zinc; ammonia and organic amines such as non-substituted or hydroxy-substituted mono-, di- or trialkylarnines; dicyclohexylamines; tributyl amines; pyridine; N-methyl-N-ethylamine; diethylamine; triethylamine; mono-, bis- or tris-(2-hydroxy-alkylarnines) such as mono-, bis- or tris-(2-hydroxyethyl)amine, 2-hydroxy-tert-butylarnine ortris-(hydroxymethyl)methylamine, N,N-di-alkyl-N-(hydroxyalkyl)-amines, such as N,N-dimethyl-N-(2-hydroxyethyl)amine or tri-(2-hydroxyethyl)arnine; N-methyl-D-glucamine; and amino acids such as arginine and lysine.

According to a preferred form of the invention, at least one of the X1, X2, X3, X4, X5, Xa, Xb, Xc, Xd, Xe and Xf radicals is O.

According to a preferred form of the invention, at least one of the Y1, Y2, Y3, Y4, Y6 radicals, independently, designates H.

According to a preferred form of the invention, at least one of the Y1, Y2, Y3, Y4, Y6 radicals, independently, designates CH3.

According to a preferred form of the invention, R1 designates H or CH3.

According to a preferred form of the invention, n is equal to 5.

According to a particularly preferred form, the composition of the invention comprises Baicalin that satisfies the following general formula (II):

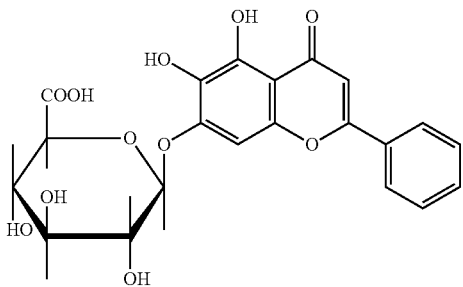

(II)

or a plant extract that comprises it.

This compound is in particular described in the application WO2008/140440 particularly in solution form. Baicalin may be used in solution form comprising a glycol alkyl having 2 to 7 carbon atoms, a polyol ether, and at least one anti-oxidant. Such an organic compound may be obtained as described in EP1400579 (US2004/0067894) relating to the synthesis of tetrahydroxyflavones wherein the general formula comprises Baicalin.

Baicalin may be used in the form of an extract of plant origin. Baicalin is a polyphenol (flavone) particularly extracted from skull cap root, in particular from *Scutellaria baicalensis*) with INCI name: SCUTELLARIA BAICALENSIS ROOT EXTRACT. It comes from traditional Chinese medicine. The various modes for preparing extracts are described in application WO2005044281.

Baicalin is in particular available from MMP under the trade name BAICALIN 95 MM® from MMP.

Baicalin and/or one of its derivatives or a plant extract containing it, in particular Baicalin having formula (II) and/or one of the compounds having formula (I) is present in concentrations of active substance ranging from 0.01% to 5% by weight, better from 0.01% to 2% by weight, and more preferably from about 0.01% to about 0.5% by weight with respect to the total weight of the composition.

Superabsorbent Polymers

The composition according to the invention can comprise at least one superabsorbent polymer. A "superabsorbent polymer" means a polymer that in its dry state, is capable of spontaneously absorbing at least 20 times its own weight of aqueous fluid, and particularly water and especially distilled water. Such superabsorbents are described in the book "Absorbent polymer technology, Studies in polymer science 8" by L. BRAN NON-PAPPAS and R. HARLAND, published by Elsevier, 1990.

These polymers have high capacity for the absorption and retention of water and aqueous fluids. After absorption of the aqueous liquid, the polymer particles thus soaked in aqueous fluid remain insoluble in the aqueous fluid and thus retain their individualized particulate state.

The superabsorbent polymer can have a water absorption capacity varying from 20 to 2000 times its own weight (namely 20 g à 2000 g of water absorbed per gram of absorbent polymer), preferably from 30 to 1500 times, and better from 50 to 1000 times. These water absorption characteristics are defined under normal temperature (25° C.) and pressure (760 mm Hg equal to 100000 Pa) conditions and for distilled water.

The value of the water absorption capacity of a polymer can be determined by dispersing 0.5 g of polymer(s) in 150 g of a solution of water, waiting for 20 minutes, filtering the solution not absorbed on a 150 μm filter for 20 minutes and weighing the non-absorbed water.

The superabsorbent polymer used in the composition of the invention is in the form of particles. Preferably, the superabsorbent polymer, in the dry or non-hydrated state, has an average size less than or equal to 100 μm, preferably less than or equal to 50 μm, varying for example from 10 to 100 μm, preferably from 15 to 50 μm, and even more preferably from 20 to 30 μm.

The average size of particles corresponds to the average mass diameter (D50) measured by laser size grading or another equivalent method known to an expert in the subject.

These particles, once hydrated, inflate by forming soft particles with an average size that can vary from 10 μm to 1000 μm, preferably from 20 μm to 500 μm, and even more preferably from about 50 μm to 400 μm.

Preferably, the superabsorbent polymers used in this invention are in the form of spherical particles.

In particular, the absorbent polymers are chosen from among:
- cross-linked sodium polyacrylates for example like those marketed under trade names Octacare X100, X110 and RM100 by the Avecia company, those marketed under the trade names Flocare GB300 and Flosorb 500 by the SNF company, those marketed under the trade names Luquasorb 1003, Luquasorb 1010, Luquasorb 1280 and Luquasorb 1110 by the BASF company, those marketed under the trade names Water Lock G400 and G430 (INCI name: Acrylamide/Sodium acrylate copolymer) by the Grain Processing company, or AQUA-KEEP® 10 SH—NFC (INCI name: Sodium acrylates crosspolymer-2 (and) water (and) silica) marketed by the Sumitomo Seika company,
- starches grafted by an acrylic polymer (homopolymer or copolymer) and particularly by sodium polyacrylate, like those marketed under the Sanfresh ST-100MC trade name by the Sanyo Chemical Industries company or Makimousse 25, Makimousse 12 by the Daito Kasei company (INCI name Sodium polyacrylate Starch),
- hydrolyzed starches grafted by an acrylic polymer (homopolymer or copolymer) and particularly the sodium acryloacrylamide/acrylate copolymer, like those marketed under the trade names Water Lock A-240, A-180, B-204, D-223, A-100, C-200, D-223, by the Grain Processing company (INCI name: Starch/acrylamide/sodium acrylate copolymer),
- polymers based on starch, gum and cellulose derivative, like those containing starch, guar gum and sodium carboxymethyl cellulose, marketed under the trade name Lysorb 220 by the Lysac company,
- and mixtures thereof.

The superarbsorbent polymers used in this invention may or may not be cross-linked. They are preferably chosen from among cross-linked polymers.

The superabsorbent polymers used in this invention are preferably cross-linked acrylic homo- or copolymers, preferably neutralized in particulate form.

Preferably, the superabsorbent polymer is chosen from among cross-linked sodium polyacrylates, preferably in the form of particles with an average size (or average diameter) less than or equal to 100 microns, also preferably in the form of spherical particles. These polymers preferably have a water absorption capacity equal to 10 to 100 g/g, preferably from 20 to 80 g/g and more preferably from 30 to 80 g/g.

The superabsorbent polymer(s) can be present in the composition according to the invention with a total content of active material ranging from 0.01% to 1.5% by weight, and preferably from 0.01% to 1% by weight, and more preferably from 0.1% to 0.6% by weight in relation to the total weight of the composition.

At Least Partially Neutralized Superabsorbent Acrylic Homo- and Copolymers

The composition according to the invention comprises at least one non-superabsorbent acrylic acid homo- or copolymer that is at least partially neutralized, and All non-superabsorbent acrylic acid homo- or copolymers can be used with this invention, provided that they are hydrophilic and are used in at least partially neutralized form. In the framework of the invention, a non-superabsorbent polymer is a polymer that does not comply with the definition given above for superabsorbent polymers.

For the purposes of this invention, "hydrophilic polymer" means a polymer that is soluble or dispersible in water at 25°

C. Non-superabsorbent acrylic homo- or copolymers suitable for this invention may be present in the composition in particulate or non-particulate form.

When they are present in particulate form, their average size in the hydrated state is preferably less than or equal to 10 μm, and even more preferably less than or equal to 5 μm. Their average size in the dry or non-hydrated state is preferably less than or equal to 2 μm, and more preferably less than or equal to 1 μm.

Preferable, the at least partially neutralized non-superabsorbent acrylic acid homo-or copolymer according to the invention is present in non-particulate form.

Preferably, a non-superabsorbent acrylic acid homopolymer that is at least partially neutralized is used The homopolymer used in this invention is chosen particularly among sodium polyacrylates and potassium polyacrylates. Sodium polyacrylate is used in preference.

Non-superabsorbent acrylic polymers that are neutralized before their use include for example:
- sodium polyacrylates such as those marketed under the trade name Cosmedia SP® containing 90% of dry material and 10% of water, or Cosmedia SPL® in inverse emulsion containing about 60% of dry active material, an oil (hydrogenated polydecene) and a surfactant (PPG-5 Laureth-5), both sold by the Cognis company;
- partially neutralized sodium polyacrylates, particularly in the form of an inverse emulsion comprising at least one polar oil, for example that sold under the trade name Luvigel® EM by the BASF company; and
- mixtures thereof.

A non-superabsorbent acrylic acid polymer that is not previously neutralized can also be used, and in this case it is neutralized before use by any appropriate means and particularly the addition of soda. This results in sodium polyacrylates. Potassium polyacrylates are also suitable for this invention.

On the other hand, for some of them, neutralization is inherent to the raw material. This is the case particularly for Luvigel® EM and products called Cosmedia® SP and SPL that are already partially neutralized. The neutralization step, for example by sodium or potassium counter ions, is important to confer gelling properties on acid polymers, and therefore for stabilization of the composition. Said acrylic polymers are converted into corresponding acrylate polymers during this neutralization step. Acrylic monomers of the acrylic polymer according to the invention can be neutralized from 5% to 100%, and particularly from 5% to 80%. Thus, preferably, an acrylic acid homopolymer neutralized to a content of 5% to 100% is used, and particularly from 5% to 80%.

According to one particular embodiment, the acrylic acid homo- or copolymer can be found in the form of a water-in-oil emulsion, called an inverse emulsion. For example, this inverse emulsion can be obtained by polymerization in inverse emulsion.

According to one particular embodiment of the invention, the polymer used is a partially neutralized sodium polyacrylate in the form of an inverse emulsion comprising at least one polar oil.

Fatty acid esters can be mentioned as suitable oils. Examples of these fatty acid esters include fatty acid isopropylic esters such as isopropyl palmitate or isopropyl myristate or fatty acid polyglycerides, particularly mixes of fatty acids containing at least 50% of capric and/or caprylic acids-. Such water-in-oil emulsions are described in document U.S. Pat. No. 6,197,283. According to this embodiment, the oily phase may be composed of one or several fatty acid esters, one or several fatty acid polyglycerides based on a mixture of polyglycerides, containing diglycerides and triglycerides, with mixes of fatty acids that contain caprylic acid and/or capric acid, preferably with a content of at least 50% by weight relative to the total weight of fatty acids.

According to one embodiment of the invention, the oil content of the inverse emulsion is between 15% and 70% by weight, particularly between 20% and 35% by weight relative to the total weight of the inverse emulsion. In this respect, Luvigel® EM in particular can be mentioned, for which the oily phase comprises 26% of oil phase composed of C8-10 triglycerides, namely for which the fatty acids are a mixture of capric acid and caprylic acid.

Furthermore, the water-in-oil emulsion can contain 0.25% to 7% by weight, preferably 0.5% to 5% by weight, of a surfactant.

The at least partially neutralized acrylic polymer can be present in the inverse emulsion with a total content ranging from 20% to 70% by weight, particularly from 20% to 65% by weight, and for example from 20% to 62% by weight in relation to the total weight of the inverse emulsion.

In particular, according to one embodiment, the acrylic polymer may be present in the inverse emulsion with a content varying from 20% to 30% by weight relative to the total weight of the inverse emulsion.

According to yet another embodiment, the acrylic polymer may be present in the inverse emulsion with a content varying from 50% to 62% by weight relative to the total weight of the composition.

The hydrophilic acrylic homo- or copolymers can be present in the composition according to the invention with a content of active material ranging for example from 0.02% to 2% by weight, preferably from 0.1% to 1.5% by weight, and even more preferably from 0.3% to 1% by weight in relation to the total weight of the composition.

Advantageously, in compositions according to the invention, the ratio by weight between the acrylic homo- or copolymer (compound c) and the superabsorbent polymer (compound b) may be between 1 and 2. Preferably, said ratio by weight is between 1.3 and 1.9, even more preferably between 1.4 and 1.8.

In particular, this ratio by weight between the acrylic homo- or copolymer (compound c) and the superabsorbent polymer (compound b) enables good stabilization of the compositions. pH of the composition The pH of the composition according to the invention is 6.0 to 6.5. Advantageously, the pH of the composition is between 6.1 and 6.4.

According to one alternative embodiment, the cosmetic composition according to the invention may comprises an acid and a base.

According to one alternative embodiment, the composition according to the invention may comprise at least one base.

The base is used particularly to increase the pH of the initial aqueous solution comprising baicalin and consequently solubility same. It may also be used to adjust the final pH of the composition to between 6.0 and 6.5, preferably between 6.1 and 6.4.

The base may be chosen from mineral bases such as for example alkaline metal hydroxides, sodium hydroxide, potassium hydroxide, ammonium hydroxides, ammonia, organic bases such as for example monoethanolamine, diethanolamine, triethanolamine, triisopropylamine, tri[(2-hydroxy) 1-propyl)] amine, N,N-dimethyl ethanolamine, 2-amino 2-methyl 1-propanol, 2-amino 2-methyl 1,3-propanediol, triethylamine, dimethylaminopropylamine and amphoteric bases (i.e. bases having both anionic and cationic functional groups) such as primary, secondary, tertiary or cyclic organic amines, amino acids. By way of example of amphoteric bases, mention may be made of glycine, lysine, arginine, taurine, histidine, alanine, valine, cysteine, trihydroxymrehylaminomethane (TRISTA), triethanolamine and any of the mixtures thereof.

According to one particular embodiment, the base of the composition is chosen from sodium hydroxide, potassium hydroxide, ammonium hydroxides, ammonia, monoethanolamine, diethanolamine, triethanolamine, tromethamine and any of the mixtures thereof. According to one particular embodiment, the base of the composition is chosen from among sodium hydroxide, triethanolamine, and mixtures thereof.

According to one particular embodiment, the base of the composition according to the invention is present at a mass concentration less than 0.5%, or less than 0.25% by mass with respect to the total mass of the composition.

According to one alternative embodiment, the composition according to the invention may comprise at least one acid. It may be used to adjust the final pH of the composition to between 6.0 and 6.5, and preferably between 6.1 and 6.4.

The acid may be chosen from inorganic acids such as hydrochloric acid, sulfuric acid, nitric acid, organic acids such as acetic acid, lactic acid, glycolic acid, mandelic acid, citric acid, ascorbic acid and any of the mixtures thereof.

The acid may be chosen from among organic acids such as stearic acid, palmitic acid, myristic acid and any mixture thereof.

According to one particular embodiment, the acid of the composition according to the invention is present at a mass concentration less than 0.5%, or less than 0.25% by mass with respect to the total mass of the composition.

Aqueous Phase

The composition according to the invention comprises a physiologically acceptable aqueous medium. "Physiologically acceptable" means a medium compatible with keratin materials.

The composition according to the invention preferably comprises an aqueous medium comprising water and possibly an organic solvent soluble in water at 25° C., chosen for example from among linear or branched alkanols, in C2-C4, such as ethanol and isopropanol, propanol, butanol; polyols particularly with 2 to 20 carbon atoms, preferably 2 to 6 carbon atoms such as glycerol, diglycerol, propyleneglycol, glycol isoprene, dipropyleneglycol, butylene glycol, hexylene glycol, 1,3-propanediol, pentylene glycol, polyethyleneglycols with 2 to 200 ethylene oxide motifs, and mixtures thereof.

The composition generally comprises from 10% to 95% by weight of water with respect to the total weight of the composition and preferably from 30% to 80%.

The quantity of organic solvents can range for example from 0% to 30% by weight, preferably from 0.5% to 25% by weight, better from 5% to 20% by weight, even better from 10% to 22% by weight relative to the total weight of the composition.

The composition according to the invention is an oil-in-water emulsion.

Surfactant

The O/W emulsion according to the invention includes a gemini surfactant with formula (III):

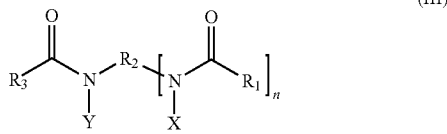

wherein:
R1 and R3 designate, independently of each other, an alkyl radical with 1 to 25 carbon atoms;
R2 designates a spacer comprised of a linear or branched alkylene chain with from 1 to 12 carbon atoms;
X and Y, independently of each other, designate a —(C2H4O)a—(C3H6O)bZ group in which
Z designates a hydrogen atom or a —CH2-COOM, —SO3M, —P(O)(OM)2, —C2H4-SO3M, —C3H6-SO3M or —CH2(CHOH)4CH2OH radical, in which M represents H or an alkali ion or an alkali earth ion or ammonium or alkanolammonium,
a varies from 0 to 15,
x varies from 0 to 10; and
the sum of a+b varies from 1 to 25; and
n varies from 1 to 10.

The gemini surfactant with formula (III) is preferably such that each of the R1-CO— and R3-CO— groups comprises from 8 to 20 carbon atoms, and preferably designates a residue of coconut fatty acids (comprising particularly lauric acid and myristic acid).

Furthermore, this surfactant is preferably such that, for each of the X and Y radicals, the sum of a and b has an average value that varies from 10 to 20 and is preferably equal to 15. A preferred group for Z is the —SO3M group, where M is preferably an alkali ion such as a sodium ion.

The spacer R2 is advantageously composed of a C1-C3 linear alkylene chain and preferably an ethylene chain (CH2CH2).

Finally, n is advantageously equal to 1.

A surfactant of this type is identified particularly by the INCI name Sodium dicocoylethylenediamine PEG-15 sulfate, with the following structure:

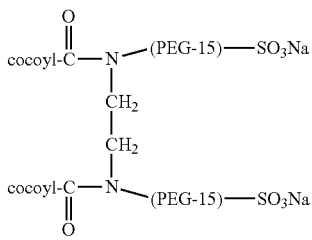

with the understanding that PEG represents the —CH2CH2O-group and that 'cocoyl' represents the coconut fatty acid residue.

This surfactant has a molecular structure that is very similar to that of ceramide-3.

Preferably, the gemini surfactant with formula (III) is used in a mixture with other surfactants, and in particular in a mixture with (a) a C6-C22 fatty acid ester (preferably C14-C20 such as stearate) and glyceryl, (b) a C6-C22 fatty acid diester (preferably C14-C20 such as a stearate) and citric acid and glycerol (in particular a C6-C22 fatty acid diester and glyceryl monocitrate), and (c) a C10-C30 fatty alcohol (preferably behenyl alcohol).

Advantageously, the composition according to the invention comprises a mixture of sodium dicocoylethylenediamine PEG-15 sulfate, of glyceryl stearate, of glyceryl stearate monocitrate and of behenyl alcohol.

More preferably, the gemini surfactant according to the formula (III) represents from 10% to 20% by weight, and advantageously 15% by weight; the C6-C22 fatty acid and glyceryl ester represents from 30% to 40% by weight, advantageously 35% by weight; the C6-C22 fatty acid and citric acid and glycerol diester represents from 10% to 20% by weight, advantageously 15% by weight; and the C10-C30 fatty alcohol represents from 30% to 40% by weight, advantageously 35% by weight, in relation to the total weight of the surfactants mixture containing the gemini surfactant.

Advantageously, the composition according to the invention comprises a mixture of 10% to 20% (particularly 15%) by weight of sodium dicocoylethylenediamine PEG-15 sulfate, from 30% to 40% (in particular 35%) by weight of glyceryl stearate, from 10% to 20% (in particular 15%) by weight of glyceryl stearate monocitrate and from 30% to 40% (in particular 35%) by weight of behenyl alcohol, in relation to the total weight of the surfactant mixture containing the gemini surfactant.

As a variant, the gemini surfactant with formula (III) can be used in a mix with an anionic surfactant such as a lauric acid and lactyl lactate ester salt, such as sodium lauroyl lactylate. In this case, the gemini surfactant preferably represents 30% to 50% by weight, and the anionic surfactant represents 50% to 70% by weight, in relation to the total weight of the surfactants mixture.

For example, the gemini surfactant with formula (III) can be used in a mixture with other surfactants in the form of products sold by the SASOL company under the trade names CERALUTION®, and in particular the following products:
Ceralution® H: Behenyl Alcohol, Glyceryl Stearate, Glyceryl Stearate Citrate and Sodium Dicocoylethylenediamine PEG-15 Sulfate,
Ceralution® F: Sodium Lauroyl Lactylate and Sodium Dicocoylethylenediamine PEG-15 Sulfate or,
Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names).

This gemini surfactant represents from 3% to 50% by weight of these mixtures.

The gemini surfactant (III) may be present with a content ranging from 0.5% to 4% by weight, preferably from 1% to 3% by weight, even more preferably from 1.5% to 2.5% by weight, relative to the total weight of the composition.

Oily Phase

The composition according to the invention preferably comprises at least one oily phase.

When the composition used according to the invention comprises an oily phase, this oily phase preferably contains at least one oil, particularly a cosmetic oil. It may further contain other fats.

By way of oils suitable for use in the composition according to the invention, mention may be made for example of:

- hydrocarbon oils of animal origin, such as perhydrosqualene;
- hydrocarbon oils of plant origin, such as liquid fatty acid triglycerides having 4 to 10 carbon atoms such as heptanoic or octanoic acid triglycerides or, for example sunflower, corn, soybean, pumpkin, grape seed, sesame, hazelnut, apricot, macadamia, arara, sunflower, castor, avocado oils, caprylic/capric acid triglycerides such as those sold by the Stearineries Dubois company or those sold under the trade names Miglyol "810", "812" and "818" by the Dynamit Nobel company, jojoba oil, shea butter oil;
- esters and synthetic esters, in particular fatty acids, such as oils having formulas R1COOR2 and R1OR2 wherein R1 is the remainder of a fatty acid comprising from 8 to 29 carbon atoms, and R2 is a hydrocarbon chain, branched or not, containing from 3 to 30 carbon atoms, such as for example Purcellin oil, isononyl isononanoate, isopropyl myristate, ethyl-2-hexyl palmitate, octyl-2-dodecyl stearate, octyl-2-dodecyl erucate, isostearyl isostearate; hydroxylated esters such as isostearyl lactate, octylhydroxystearate, octyldodecyl hydroxystearate, diisostearyl-malate, triisocetyl citrate; heptanoates, octanoates, decanoates of fatty alcohols; polyol esters, such as propylene glycol dioctanoate, neopentyl glycol diheptanoate and diethylene glycol diisononanoate; and pentaerythritol esters such as pentaerythrityl tetraisostearate;
- linear or branched hydrocarbons, with inorganic or synthetic origin, such as volatile or non-volatile paraffin oils and derivatives thereof, hydrocarbon oils with branched chain containing 10 to 20 carbon atoms such as isohexadecane, isododecane, isoparaffins and mixtures thereof, vaseline, polydecenes, hydrogenated polyisobutene such as Parleam® oil;
- natural or synthetic essential oils, for example such as eucalyptus oil, lavandin oils, lavender oils, vetiver oil, litsea cubeba oil, lemon oil, sandalwood oil, rosemary oil, chamomile oil, savory oil, nutmeg oil, cinnamon oil, hyssop oil, caraway oil, orange oil, geraniol oil, juniper oil and bergamot oil;
- fatty alcohols having 8 to 26 carbon atoms, such as cetyl alcohol, stearyl alcohol, the mixture of cetyl alcohol and stearyl alcohol (cetylstearyl alcohol), octyl dodecanol, 2-butyloctanol, 2-hexyldecanol, 2-undecylpentadecanol, oleic acid or linoleic acid;
- partially hydrocarbon and/or silicone fluorinated oils such as those described in the document JP-A-2-295912;
- silicone oils such as polymethylsiloxanes (PDMS), optionally volatile with a linear or cyclic silicone chain, liquid or pasty at ambient temperature, particularly cyclopolydimethylsiloxanes (cyclomethicones) such as cyclohexasiloxane; polydimethylsiloxanes comprising alkyl, alkoxy or phenyl pendant or silicon chain-end groups, groups having 2 to 24 carbon atoms; phenyl silicones such as phenyltrimethicones, phenyldimethicones, phenyltrimethylsiloxydiphenyl-siloxanes, diphenyl-dimethicones, diphenylmethyldiphenyl trisiloxanes, 2-phenylethyltrimethyl-siloxysilicates, and polymethylphenylsiloxanes; or
- mixtures thereof.

The other fats suitable for being present in the oil phase are for example fatty acids comprising 8 to 30 carbon atoms, such as stearic acid, lauric acid, cetyl acid, palmitic acid and oleic acid; waxes such as lanolin, beeswax, Carnauba or Candellila wax, paraffin wax, lignite wax or microcrystalline waxes, ceresin or ozokerite, synthetic waxes such as polyethylene waxes, Fischer-Tropsch waxes; silicone resins such as trifluoromethyl-C1-4-alkyldimethicone and trifluoropropyldimethicone; and silicon elastomers such as the products marketed under the trade names "KSG" by the Shin-Etsu company, under the trade names "Trefil", "BY29" or "EPSX" by the Dow Corning company or under the trade names "Gransil" by the Grant Industries company.

These fats may be chosen in varied ways by those skilled in the art in order to prepare a composition having the sought properties, for example consistency or texture properties.

The quantity of oil phase may range for example 0.1% to 25%, and for example from 10% to 20% by weight with respect to the total weight of the composition.

Thickener

The composition according to the invention can include a thickener/oil phase structuring agent chosen from among polymers, particularly, C10 to C30 and preferably C14 to C22 alkyl (meth)acrylate homopolymers; and more particularly, poly(stearyl acrylate) or poly(behenyl acrylate) homopolymers, such as those marketed under the trade names Intelimer® IPA 13-1 NG polymer, Intelimer® IPA 13-6 by the Air Product and Chemicals company (INCI name: POLY C10-30 ALKYL ACRYLATE). Poly(stearyl acrylate) homopolymers will be preferably be used.

According to one embodiment, the quantity of thickening agent varies from 0.1% to 4%, preferably 1% to 3%, and for example 1.5% to 2.5%, by weight in relation to the total weight of the composition.

UV Filter

According to one advantageous embodiment, the composition according to the invention may further comprise at least one organic and/or inorganic UV filter (filters of UV rays from sunlight).

The UV filter is a UV filter routinely used in cosmetics. It may be chosen in the positive list contained in Annex VI of the Regulation (EC) No. 1223/2009, which specifies the list of UV filters authorized in cosmetics.

The UV filters of the composition according to the invention can be organic or inorganic. The UV filters of the composition according to the invention can provide a UVA and/or UVB photoprotection.

The composition preferably comprises at least one UV filter chosen from hydrophilic organic UV filters, lipophilic organic UV filters, insoluble organic UV filters, inorganic filters or any of the mixtures thereof.

The term "hydrosoluble UV filter" refers to any organic or inorganic cosmetic or dermatological compound that filters UV radiation that can be completely dissolved in the molecular state or made miscible in a liquid aqueous phase or be solubilized in colloidal form (for example in micellar form) in a liquid aqueous phase.

The term "liposoluble filter" refers to any organic or inorganic cosmetic or dermatological compound that filters UV radiation that can be completely dissolved in the molecular state or made miscible in an oil phase or be solubilized in colloidal form (for example in micellar form) in an oil phase.

The term "insoluble UV filter" refers to any organic or inorganic cosmetic or dermatological compound that filters UV radiation and that has a solubility of less than 0.5% by weight in water and a solubility of less than 0.5% by weight in most organic compounds such as paraffin oil, fatty alcohol benzoates and fatty acid triglycerides, for example Miglyol 812® marked by the DYNAMIT NOBEL company. This solubility at 70° C. is defined as the quantity of product in solution in equilibrium in the solvent with an excess quantity of solid in suspension after returning to ambient temperature. It can easily be evaluated in the laboratory.

a) Organic UV filters

Organic UV filters are chosen particularly among cinnamic compounds; dibenzoylmethane compounds; anthranilate compounds; salicylic compounds, dibenzoylmethane compounds, benzylidene camphor compounds; benzophenone compounds; 13,3-diphenylacrylate compounds; triazine compounds; benzotriazole compounds and particularly benzotriazoles described in patent EP0392883 and methylene bis-(hydroxyphenyl benzotriazole) compounds as described in applications U.S. Pat. Nos. 5,237,071, 5,166, 355, GB2303549, DE 197 26 184 and EP893119; benzalmalonate compounds particularly those mentioned in U.S. Pat. No. 5,624,663; benzimidazole derivatives; imidazoline compounds; bis-benzoazolyl compounds as described in patents EP669323 and U.S. Pat. No. 2,463,264; p-aminobenzoic (PABA) compounds; benzoxazole compounds as described in patent applications EP0832642, EP1027883, EP1300137 and DE10162844; filter polymers and filter silicones as described particularly in application WO-93/04665; dimers derived from oalkylstyrene as described particularly in patent application DE19855649; 4,4-diarylbutadiene compounds as described in applications EP0967200, DE19746654, DE19755649, EP-A-1008586, EP1133980 and EP133981; merocyanine compounds as described in U.S. Pat. No. 4,195,999, application WO2004/006878, applications WO2008/090066, WO2011113718, WO2009027258, WO2013010590, WO2013011094, WO2013011480 and documents IP COM JOURNAL No. 000179675D published on Feb. 23 2009, IP COM JOURNAL No 000182396D published on Apr. 29 2009, IP COM JOURNAL No. 000189542D published on Nov. 12 2009, IP COM Journal No. IPCOM000011179D published on Apr. 3, 2004 and mixtures thereof.

Examples of organic photoprotective agents include those referred to hereinafter using their INCI name:

Dibenzoylmethane Compounds
    Butyl Methoxydibenzoylmethane particularly sold under the trade name "PARSOL 1789®" by DSM Nutritional Products, Inc.;

Cinnamic Compounds:
    Ethylhexyl Methoxycinnamate particularly sold under the trade name "PARSOL MCX®" by DSM Nutritional Products
    Isopropyl Methoxycinnamate
    Isoamyl p-Methoxycinnamate particularly sold under the trade name NEO HELIOPAN E 1000 ® by Symrise
    DEA Methoxycinnamate,
    Diisopropyl Methylcinnamate,
    Glyceryl Ethylhexanoate Dimethoxycinnamate.

Para-aminobenzoic compounds:
    PABA,
    Ethyl PABA,
    Ethyl Dihydroxypropyl PABA,
    Ethylhexyl Dimethyl PABA particularly sold under the name "ESCALOL 507®" by ISP, Glyceryl PABA,
    PEG-25 PABA sold under the name "UVINUL P25®" by BASF.

Salicylic Compounds:
    Homosalate sold under the name "Eusolex HMS®" by Rona/EM Industries;
    Ethylhexyl Salicylate sold under the name "NEO HELIOPAN OS®" by Symrise,
    Dipropyleneglycol Salicylate sold under the name "DIPSAL®" by SCHER,
    TEA Salicylate sold under the name "NEO HELIOPAN TS®" by Symrise, $\beta,\beta$-diphenylacrylate compounds:
    Octocrylene particularly sold under the trade name "UVINUL 539®" by BASF,
    Etocrylene, particularly sold under the trade name "UVINUL N35®" by BASF, Benzophenone Compounds:
    Benzophenone-1 sold under the trade name "UVINUL 400®" by BASF,
    Benzophenone-2 sold under the trade name "UVINUL 50®" by BASF;
    Benzophenone-3 or Oxybenzone, sold under the trade name "UVINUL M 40®" by BASF,
    Benzophenone-4 sold under the trade name "UVINUL MS 40®" by BASF,
    Benzophenone-5
    Benzophenone-6 sold under the trade name "Helisorb 11®" by Norquay
    Benzophenone-8 sold under the trade name "Spectra-Sorb UV-24®" by American Cyanamid;
    Benzophenone-9 sold under the trade name "UVINUL DS 49®" by BASF,
    Benzophenone-12
    n-hexyl 2-(4-diethylamino-2-hydroxybenzoyl)-benzoate sold under the trade name "UVINUL A Plus®" or mixed with octylmethoxycinnamate sold under the trade name "UVINUL A Plus B®" by the BASF company,
    1,1'-(1,4-piperazinediyl)bis[1-[2-[4-(diethylamino)-2-hydroxybenzoyl]phenyl]-methanone (CAS 919803-06-8) as described in application WO2007/071584; this compound advantageously being used in micronized form (average size from 0.02 to 2 µm) that can be obtained for example using the micronization method described in applications GB-A-2 303 549 and EP-A-893119 and particularly in the form of an aqueous dispersion.

Benzylidene Camphor Compounds:
    3-Benzylidene camphor manufactured under the name "MEXORYL SD®" by CHIMEX,
    4-Methylbenzylidene camphor sold under the name "EUSOLEX 6300®" by MERCK,
    Benzylidene Camphor Sulfonic Acid manufactured under the name "MEXORYL SL®" by CHIMEX,
    Camphor Benzalkonium Methosulfate manufactured under the name "MEXORYL SO®" by CHIMEX,
    Terephthalylidene Dicamphor Sulfonic Acid manufactured under the name "MEXORYL SX®" by CHIMEX.
    Polyacrylamidomethyl Benzylidene Camphor manufactured under the name "MEXORYL SW®" by CHIMEX.

Phenyl Benzimidazole Compounds:
    Phenylbenzimidazole Sulfonic Acid particularly sold under the trade name "EUSOLEX 232®" by MERCK.

Bis-Benzoazolyl Compounds
    Disodium Phenyl Dibenzimidazole Tetrasulfonate sold under the trade name "NEO HELIOPAN AP®" by Symrise.

Benzotriazole Compounds
    Drometrizole Trisiloxane manufactured under the name "MEXORYL SX®" by CHIMEX, Methylene bis-Benzotriazolyl Tetramethylbutylphenol particularly sold in solid form as the product sold under the trade name "MIXXIM BB/100®" by FAIRMOUNT CHEMICAL or in the form of an aqueous dispersion of micronized particles with an average particle size varying from 0.01 to 5 µm and preferably from 0.01 to 2 µm and more particularly from 0.020 to 2 µm with at least one alkylpolyglycoside surfactant with a $C_nH_{2n+1}O$ $(C_6H_{10}O_5)_xH$ structure in which n is an integer from 8 to 16 and x is the average degree of polymerization of the $(C_6H_{10}O_5)$ unit and varies from 1.4 to 1.6 as described in patent GB-A-2 303 549 particularly sold under the trade name "TINOSORB M®" by the BASF company or in the form of an aqueous dispersion of micronized particles with an average particle size varying from 0.02 to 2 µm and preferably from 0.01 to 1.5 µm and more particularly from 0.02 to 1 µm in the presence of at least one polyglycerol mono-$(C_8-C_{20})$ alkyl-ester with a degree of polymerization of glycerol of at least 5 such as aqueous dispersions described in application WO2009/063392.

Triazine Compounds:
 Bis-Ethylhexyloxyphenol Methoxyphenyl Triazine sold under the trade name "TINOSORB S®" by BASF,
 Ethylhexyl Triazone particularly sold under the trade name "T150®" by BASF,
 Diethylhexyl Butamido Triazone sold under the trade name "UVASORB HEB®" by SIGMA 3V,
 2,4,6-tris(dineopentyl 4'-amino benzalmalonate)-s-triazine,
 2,4,6-tris(diisobutyl 4'-amino benzalmalonate)-s-triazine,
 2,4-bis (n-butyl 4'-aminobenzoate)-6-(aminopropyl trisiloxane)-s-triazine,
 2,4-bis(dineopentyl 4'-amino benzalmalonate)-6-(n-butyl 4'-aminobenzoate)-s-triazine;
 symmetric triazine filters substituted by naphthalenyl groups or polyphenyl groups described in U.S. Pat. No. 6,225,467, application WO2004/085412 (see compounds 6 and 9) or document "Symmetrical Triazine Derivatives" IP.COM IPCOM000031257 Journal, INC WEST HENRIETTA, N.Y., US (Sep. 20 2004) particularly 2,4,6-tris(di-phenyl)-triazine and 2,4,6-tris(ter-phenyl)-triazine that is included in patent applications WO06/035000, WO06/034982, WO06/034991, WO06/035007, WO2006/034992, WO2006/034985, these compounds advantageously being in micronized form (average particle size from 0.02 to 3 µm) that can for example be obtained using the micronization process described in applications GB-A-2 303 549 and EP-A-893119 and particularly in an aqueous dispersion;
 triazine silicones substituted by two aminobenzoate groups as described in patent EP0841341 and particularly 2,4-bis-(n-butyl 4'-aminobenzalmalonate)-6-[(3-{1,3,3,3-tetramethyl-1-[(trimethylsilyloxy]disiloxanyl}propyl)amino]-s-triazine.

Anthranilic Compounds:
 Menthyl anthranilate sold under the trade name "NEO HELIOPAN MA®" by Symrise, Imidazoline Compounds:
 Ethylhexyl Dimethoxybenzylidene Dioxoimidazoline Propionate, Benzalmalonate Compounds:
 Polyorganosiloxane with benzalmalonate functions such as Polysilicone-15 sold under the trade name "PARSOL SLX®" by DSM Nutritional Products, Inc.

4,4-diarylbutadiene Compounds:
 1,1-dicarboxy (2,2'-dimethyl-propyl)-4,4-diphenylbutadiene:

Benzoxazole Compounds:
 2,4-bis-[5-1 (dimethylpropyl)benzoxazol-2-yl-(4-phenyl)-imino]-6-(2-ethylhexyl)-imino-1,3,5-triazine sold under the trade name Uvasorb K2A® by Sigma 3V.

Preferred organic filters are chosen from
 Butyl Methoxydibenzoylmethane
 Ethylhexyl Methoxycinnamate
 Ethylhexyl Salicylate,
 Homosalate
 Octocrylene
 Phenylbenzimidazole Sulfonic Acid,
 Benzophenone-3,
 Benzophenone-4,
 Benzophenone-5,
 n-hexyl 2-(4-diethylamino-2-hydroxybenzoyl)-benzoate.
 4-Methylbenzylidene camphor,
 Terephthalylidene Dicamphor Sulfonic Acid,
 Disodium Phenyl Dibenzimidazole Tetra-sulfonate,
 Methylene bis-Benzotriazolyl Tetramethylbutylphenol
 Bis-Ethylhexyloxyphenol Methoxyphenyl Triazine
 Ethylhexyl triazone,
 Diethylhexyl Butamido Triazone,
 2,4,6-tris(dineopentyl 4'-amino benzalmalonate)-s-triazine
 2,4,6-tris(diisobutyl 4'-amino benzalmalonate)-s-triazine
 2,4-bis-(n-butyl 4'-aminobenzoate)-6-(aminopropyl trisiloxane)-s-triazine,
 2,4-bis(dineopentyl 4'-amino benzalmalonate)-6-(n-butyl 4'-aminobenzoate)-s-triazine,
 2,4-bis-(n-butyl 4'-aminobenzalmalonate)-6-[(3-{1,3,3,3-tetramethyl-1-[(trimethylsilyloxy]disiloxanyl}propyl)amino]-s-triazine,
 2,4,6-tris-(di-phenyl)-triazine,
 2,4,6-tris-(ter-phenyl)-triazine,
 Drometrizole Trisiloxane
 Polysilicone-15
 1,1-dicarboxy (2,2'-dimethyl-propyl)-4,4-diphenylbutadiene
 2,4-bis-[5-1 (dimethylpropyl)benzoxazol-2-yl-(4-phenyl)-imino]-6-(2-ethylhexyl)-imino-1,3,5-triazine
 and mixtures thereof.

Particularly preferred organic filters are chosen from
 Butyl Methoxydibenzoylmethane
 Ethylhexyl Salicylate,
 Homosalate
 Octocrylene
 n-hexyl 2-(4-diethylamino-2-hydroxybenzoyl)-benzoate.
 Terephthalylidene Dicamphor Sulfonic Acid,
 Bis-Ethylhexyloxyphenol Methoxyphenyl Triazine
 Ethylhexyl triazone,
 Diethylhexyl Butamido Triazone,
 2,4-bis-(n-butyl 4'-aminobenzalmalonate)-6-[(3-{1,3,3,3-tetramethyl-1-[(trimethylsilyloxy]disiloxanyl}propyl)amino]-s-triazine,
 Drometrizole Trisiloxane
 and mixtures thereof.

b) Inorganic UV Filters

Inorganic UV filter used in accordance with this invention are metallic oxide pigments. Inorganic UV filters used in accordance with this invention are preferably metallic oxide particles with an average elementary particle size of less than or equal to 0.5 µm, more preferably between 0.005 and 0.5 µm and even more preferably between 0.01 and 0.2 µm, even better between 0.01 and 0.1 µm, and especially between 0.015 and 0.05 µm.

They can be chosen particularly among titanium, zinc, iron, zirconium and cerium oxides or mixtures thereof.

Such pigments of metal oxides, coated or not coated, are described particularly in patent application EP-A-0 518 773. Commercial pigments include products sold by the SACHTLEBEN PIGMENTS, TAYCA, MERCK AND DEGUSSA companies.

The metal oxide pigments may be coated or uncoated.

Coated pigments are pigments on which one or several chemical, electronic, mechanochemical and/or mechanical surface treatments have been made using compounds such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, oxides of metals or sodium hexametaphosphate.

The coated pigments are particularly titanium oxides coated with:
- silica such as the product "SUNVEIL®" from the IKEDA company,
- silica and iron oxide such as the "SUNVEIL F®" product from the IKEDA company,
- silica and alumina such as the "MICROTITANIUM DIOXIDE MT 500 SA®" and "MICROTITANIUM DIOXIDE MT 100 SA" products from the TAYCA company, "TIOVEIL" from the TIOXIDE company,
- alumina such as the "TIPAQUE TTO-55 (B)®" and "TIPAQUE TTO-55 (A)@" products from the ISHIHARA company, and "UVT 14/4" from the SACHTLEBEN PIGMENTS company,
- alumina and aluminum stearate such as the "MICROTITANIUM DIOXIDE MT 100 T®, MT 100 TX@, MT 100 Z®, MT-01®" products from the TAYCA company, the "Solaveil CT-10 W®" and "Solaveil CT 100®" products from the UNIQEMA company and the "Eusolex T-AVO®" product from the MERCK company,
- silica, alumina and alginic acid such as the "MT-100 AQ®" product from the TAYCA company,
- alumina and aluminum laurate such as the "MICROTITANIUM DIOXIDE MT 100 S®" product from the TAYCA company,
- iron oxide and iron stearate such as the "MICROTITANIUM DIOXIDE MT 100 F®" product from the TAYCA company,
- zinc oxide and zinc stearate such as the "BR 351®" product from the TAYCA company,
- silica and alumina treated with a silicone such as the "MICROTITANIUM DIOXIDE MT 600 SAS®", "MICROTITANIUM DIOXIDE MT 500 SAS®" or "MICROTITANIUM DIOXIDE MT 100 SAS®" products from the TAYCA company,
- silica, alumina, aluminum stearate treated with a silicone such as the "STT-30-DS®" product from the TITAN KOGYO company,
- silica treated with a silicone such as the "UV-TITAN X 195®" product from the SACHTLEBEN PIGMENTS company.
- alumina treated with a silicone such as the "TIPAQUE TTO-55 (S)®" product from the ISHIHARA company, or the "UV TITAN M 262®" product from the SACHTLEBEN PIGMENTS company,
- triethanolamine such as the "STT-65-S" product from the TITAN KOGYO company,
- stearic acid such as the "TIPAQUE TTO-55 (C)®" product from the ISHIHARA company, sodium hexametaphosphate such as the "MICROTITANIUM DIOXIDE MT 150 W®" product from the TAYCA company.
- $TiO_2$ treated by octyl trimethyl silane sold under the trade name "T 805®" by the DEGUSSA SILICES company,
- $TiO_2$ treated by a polydimethylsiloxane sold under the trade name "70250 Cardre UF $TiO_2SI3$®" by the CARDRE company,
- $TiO_2$ anatase/rutile treated by a polydimethylhydrogenosiloxane sold under the trade name "MICRO TITANIUM DIOXIDE USP GRADE HYDROPHOBIC®" by the COLOR TECHNIQUES company.

We can also mention TiO2 pigments doped with at least one transition metal such as iron, zinc, manganese and especially manganese. Preferably, said doped pigments are in the form of an oily dispersion. The oil present in the oily dispersion is preferably chosen from among triglycerides including capric/caprylic acid triglycerides. The oily dispersion of titanium oxide particles may comprise one or several dispersing agents for example such as a sorbitan ester such as sorbitan isostearate, a fatty acid ester and a polyoxyalkylene glycerol such as TRI-PPG3 MYRISTYLETHER CITRATE and POLYGLYCERYL-3 POLYRICINOLEATE. Preferably, the oily dispersion of titanium oxide particles comprises at least one dispersing agent chosen from among fatty acid esters and polyoxyalkylene glycerol. In particular, we can mention the oily dispersion of TiO2 particles doped with manganese in capric/caprylic acid triglyceride in the presence of TRI-PPG-3 MYRISTYLETHER CITRATE and POLYGLYCERYL-3-POLYRICINOLEATE and SORBITAN ISOSTEARATE with INCI name: TITANIUM DIOXIDE (and) TRI-PPG-3 MYRISTYLETHER CITRATE (and) POLYGLYCERYL-3 RICINOLEATE (and) SORBITAN ISOSTEARATE like the product sold under the trade name OPTISOL TD50® by the CRODA company.

The uncoated titanium oxide pigments are for example sold by the TAYCA company under the trade names "MICROTITANIUM DIOXIDE MT 500 B" or "MICROTITANIUM DIOXIDE MT600 B®", by the DEGUSSA company under the trade name "P 25", by the WACKHER company under the trade name "Oxyde de titane transparent PW®", by the MIYOSHI KASEI company under the trade name "UFTR®", by the TOMEN company under the trade name "ITS®" and by the TIOXIDE company under the trade name "TIOVEIL AQ".

Uncoated zinc oxide pigments are for example:
- those marketed under the trade name "Z-cote" by the Sunsmart company;
- those marketed under the trade name "Nanox®" by the Element is company;
- those marketed under the trade name "Nanogard WCD 2025®" by the Nanophase Technologies company;

Coated zinc oxide pigments are for example:
- those marketed under the trade name "CS-5 Zinc Oxide®" by the Toshibi company (ZnO coated with polymethylhydrogen siloxane);
- those marketed under the trade name "Nanogard Zinc Oxide FN®" by the Nanophase Technologies company (in 40% dispersion in Finsolv TN@, $C_{12}$-$C_{15}$ alcohol benzoate);
- those marketed under the trade name "DAITOPERSION ZN-30®" and "DAITOPERSION Zn-50®" by the Daito company (dispersions in cyclopolymethylsiloxane/oxyethylenated polydimethylsiloxane, containing 30% or 50% of zinc oxides coated with silica and polymethylhydrogen siloxane);
- those marketed under the trade name "NFD Ultrafine ZnO®" by the Daikin company (ZnO coated with perfluoroalkyl phosphate and perfluoroalkylethyl-based copolymer in dispersion in cyclopentasiloxane);

those marketed under the trade name "SPD-Z1®" by the Shin-Etsu company (ZnO coated with silicone-grafted acrylic polymer, dispersed in cyclodimethylsiloxane);

those marketed under the trade name "Escalol Z100®" by the ISP company (ZnO treated with alumina and dispersed in the ethylhexyl methoxycinnamate/PVP-hexadecene copolymer/methicone mixture);

those marketed under the trade name "Fuji ZnO-SMS-10®" by the Fuji Pigment company (ZnO coated with silica and polymethylsilsesquioxane);

those marketed under the trade name "Nanox Gel TN@" by the Elementis company (ZnO in 55% dispersion in C12-C15 alcohol benzoate with hydroxystearic acid polycondensate).

The uncoated cerium oxide pigments can for example be those sold under the trade name "COLLOIDAL CERIUM OXIDE®" by the RHONE POULENC company.

The uncoated iron oxide pigments are for example sold by the ARNAUD company under the trade names "NANOGARD WCD 2002® (FE 45B®)", "NANOGARD IRON FE 45 BL AQ", "NANOGARD FE 45R AQ®", "NANOGARD WCD 2006 (FE 45R®)", or by the MITSUBISHI company under the trade name "TY-220®".

The coated iron oxide pigments are for example sold by the ARNAUD company under the trade names "NANOGARD WCD 2008 (FE 45B FN)®", "NANOGARD WCD 2009® (FE 45B 556®)", "NANOGARD FE 45 BL 345®", "NANOGARD FE 45 BL®", or by the BASF company under the trade name "TRANSPARENT IRON OXIDE®".

It is also possible to cite metal oxide mixtures, particularly of titanium dioxide and cerium dioxide, including the mixture of equal weights of titanium dioxide and cerium dioxide coated with silica, sold by the IKEDA company under the trade name "SUNVEIL A®", and the mixture of titanium dioxide and zinc dioxide coated with alumina, silica and silicone such as the "M 261®" product sold by the SACHTLEBEN PIGMENTS company or coated with alumina, silica and glycerin such as the "M 211®" product sold by the SACHTLEBEN PIGMENTS company.

According to the invention, coated or uncoated titanium oxide pigments in particular are preferred.

According to one embodiment, the quantity of the UV filter or filters, present in the composition according to the invention, may range from 0.01% to 20% by weight, with respect to the total weight of the composition. It ranges for example from 1% to 20% by weight, or for example from 5% to 20% by mass, and for example ranges from 10% to 20% by mass with respect to the total mass of the composition.

According to one particular embodiment, the composition according to the invention further comprises cosmetically acceptable agents and/or excipients.

The term "cosmetically acceptable" means compatible with the skin and/or integuments thereof, having a pleasant color, odor and texture and not giving rise to unacceptable discomfort (tingling, tightness, redness), liable to dissuade the consumer from using the composition.

According to one embodiment, the composition according to the invention may further comprise at least one excipient chosen from among preservatives, fillers and mixtures thereof.

The filler may be inorganic or organic. The filler may be chosen from among synthetic or natural mica, silica powder; talc; polyamide particles, particularly those sold under the trade name ORGASOL by the Atochem company; polyethylene powders; microspheres based on acrylic copolymers, such as those made of ethylene glycol dimethacrylate/lauryl methacrylate copolymer sold by the Dow Corning company under the trade name POLYTRAP; expanded powders such as hollow microspheres and in particular, the microspheres sold under the trade name EXPANCEL by the Kemanord Plast company or under the trade name MICROPEARL F 80 ED by the Matsumoto company; silicone resin microbeads such as those sold under the trade name TOSPEARL by the Toshiba Silicone company; and mixtures thereof.

These fillers may be present in quantities ranging from 0.1% to 20% by mass and preferably from 1% to 10% by weight with respect to the total weight of the composition.

The invention also relates to the use, in particular cosmetic use, of a composition according to the invention to reduce the pigmentation induced by UV rays.

The invention also relates to a cosmetic care and/or makeup method for keratin materials, comprising the topical application of the composition according to the invention on keratin materials.

The invention also relates to a cosmetic and/or a beauty treatment method, comprising the topical application of a composition according to the invention on keratin materials. In particular, said method aims to resist or to prevent photo-induced premature ageing of keratinic materials. It can also protect keratin materials from solar radiation.

We will now give concrete examples illustrating the invention, but that are in no way restrictive.

All percentages given in the examples are given by mass, unless specified otherwise, and the temperature is ambient (20° C.) and expressed in degrees Celsius unless specified otherwise, and the pressure is atmospheric pressure, unless specified otherwise.

In the examples, quantities of the ingredients of the compositions are given as a % by weight with respect to the total weight of the composition.

Example 1: Photoprotective Cosmetic Composition Comprising Baicalin

| | |
|---|---|
| 2-ethylhexyl salicylate | 5 |
| Isononyl isononanoate | 3 |
| Cetyl alcohol | 0.75 |
| Extract of *scutellaria baicalensis* root (BAICALIN 95 MM, MMP) | 0.2 |
| Stearyl polyacrylate (Intelimer IPA 13-1, Landec) | 2 |
| Cross-linked polyacrylate microspheres (AQUAKEEP 10SH-NFC, Sumitomo Seika) | 0.4 |
| Glycerin | 7 |
| Propylene glycol | 2 |
| Sodium polyacrylate (Cosmedia SP, Cognis) | 0.7 |
| Avobenzone | 3 |
| Ethanol | 5.4 |
| Mixture of ethyldiamido-n-cocoyl sulfonate of ethoxylated sodium (15 OE)/Behenyl alcohol/glyceryl stearate/glyceryl stearate citrate (15/35/35/15) (Ceralution ® H from Sasol) | 2.5 |
| 2-ethyl hexyl 2-cyano-3,3-diphenylacrylate | 7 |
| Niacinamide | 5 |
| Water | qsp100 |

The composition is prepared using the classical emulsion preparation technique.

It has a viscosity of 50 poises measured using the protocol described above.

The ratio by weight between sodium polyacrylate (as active constituent) and cross-linked polyacrylate (as active constituent) for this composition is about 1.57.

The invention claimed is:

1. A composition in the form of an oil-in-water emulsion comprising in a physiologically acceptable aqueous medium:
   a) at least Baicalin and/or one of its derivatives or a plant extract containing it,
   b) at least one superabsorbent polymer,
   c) at least one homo- or copolymer of non-superabsorbent acrylic acid that is at least partially neutralized chosen from among sodium polyacrylates and potassium polyacrylates, and
   d) at least one gemini surfactant with formula (III):

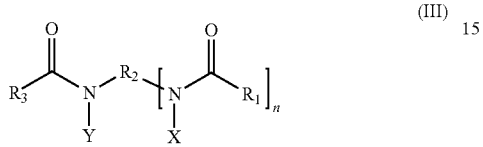

wherein:
   R1 and R3 designate, independently of each other, an alkyl radical with 1 to 25 carbon atoms;
   R2 designates a spacer comprised of a linear or branched alkylene chain with from 1 to 12 carbon atoms;
   X and Y, independently of each other, designate a —(C2H4O)a—(C3H6O)bZ group in which
   Z designates a hydrogen atom or a —CH2-COOM, —SO3M, —P(O)(OM)2, —C2H4-SO3M, —C3H6-SO3M or —CH2(CHOH)4CH2OH radical, in which M represents H or an alkali ion or an alkali earth ion or ammonium or alkanolammonium,
   a varies from 0 to 15,
   x varies from 0 to 10; and
   the sum of a+b varies from 1 to 25; and
      n varies from 1 to 10,
   said composition having a pH of 6.0 to 6.5,
   wherein the superabsorbent polymer is present in a content of active material ranging from 0.1% to 0.6% by weight with respect to the total weight of the composition, and wherein the ratio by weight between the homo- or copolymer c) and the superabsorbent polymer b) is between 1.3 and 1.9.

2. The composition according to claim 1, characterized in that it comprises an acid and a base.

3. The composition according to claim 2, wherein said Baicalin or one of the derivatives thereof is chosen from the compounds that satisfy the following formula (I):

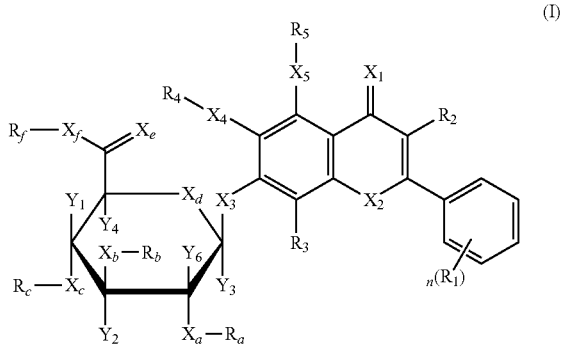

wherein
   Each X1, X2, X3, X4, X5, Xa, Xb, Xc, Xd, Xe and Xf, independently, designate O or S;
   Each Y1, Y2, Y3, Y4, Y6, independently, designates H or a (C1-C10)alkyl radical;
   Each R4, R5, Ra, Rb and Rc, independently, designates H, a (C1-C10)alkyl radial optionally substituted with 1 to 5 Ry groups, or a (C1-C10)alkyl-O—(C1-C10)alkyl radial, with each (C1-C10)alkyl radical able to be substituted with 1 to 5 Ry groups;
   Each Ry, independently, designates Rq or a —(C2-C10)alkenyl, —(C2-C10)alkynyl, —(C3-C10)cycloalkyl, —(C8-C14)bicycloalkyl, —(C8-C14)tricycloalkyl, —(C5-C10)cycloalkenyl, —(C8-C14)tricycloalkenyl, phenyl, naphthyl, —(C14)aryl radical, with each one able to be substituted with one or several Rz radicals;
   Each R1 R2, R3, independently, designates H or Rq or a —(C2-C10)alkenyl, —(C2-C10)alkynyl, —(C3-C10)cycloalkyl, —(C8-C14)bicycloalkyl, —(C8-C14)tricycloalkyl, —(C5-C10)cycloalkenyl, —(C8-C14)tricycloalkenyl, phenyl, naphthyl, —(C14)aryl radical, with each one able to be substituted with one or several Rz radicals;
   Rf is H, (C1-C12) alkyl optionally substituted with 1 to 5 Ry radicals, (C1-C12)alkyl-O—(C1-C12)alkyl, with each (C1-C12)alkyl radical able to be substituted with 1 to 5 Ry groups;
   Each Rq, independently, is CN, OH, halogen, N3, NO2, N(Rz)2, =NRz, CH=NRz, NRzOH, ORz, CORz, C(O)Rz, O(CO)ORz, SRz, S(O)Rz or S(O)2Rz;
   Each Rz, independently, is —(C1-C6)alkyl, —(C2-C6)alkenyl, —(C3-C8)cycloalkyl, —(C3-C8)cycloalkenyl, phenyl, an heterocycle having 3 to 5 branches, CH(halo)2 or C(halo)3; and
   n is 0, 1, 2, 3, 4 or 5 as well as the salts thereof, the optical isomers thereof and/or the diastereoisomers thereof.

4. The composition according to claim 1, comprising Baicalin that satisfies the following general formula (II):

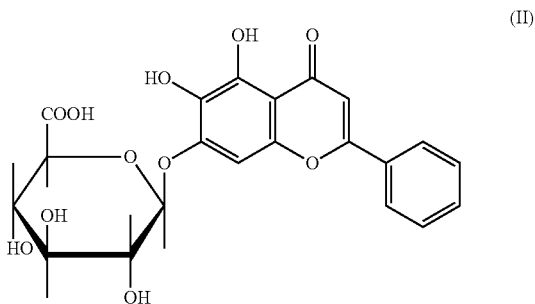

or a plant extract that contains it.

5. The composition according to claim 1, wherein said Baicalin and/or one of its derivatives or a plant extract containing it is present in concentrations of active substance ranging from 0.01% to 5% by weight with respect to the total weight of the composition.

6. The composition according to claim 1, wherein the superabsorbent polymer is chosen from among:
   cross-linked sodium polyacrylates,
   starches grafted by an acrylic polymer,
   hydrolyzed starches grafted by an acrylic polymer,
   polymers based on starch, gum and cellulose derivative, and mixtures thereof.

7. The composition according to claim 1, wherein the at least partially neutralized non-superabsorbent acrylic acid homo- or copolymer is present in a content of active material ranging from 0.02% to 2% by weight with respect to the total weight of the composition.

8. The composition according to claim 1, wherein the ratio by weight between the homo- or copolymer c) and the superabsorbent polymer b) is between 1.4 and 1.8.

9. The composition according to claim 1, wherein it further comprises at least one UV filter chosen from hydrophilic organic UV filters, lipophilic organic UV filters, insoluble organic UV filters, inorganic filters and any of the mixtures thereof.

10. The composition according to claim 1, wherein said Baicalin or one of the derivatives thereof is chosen from the compounds that satisfy the following formula (I):

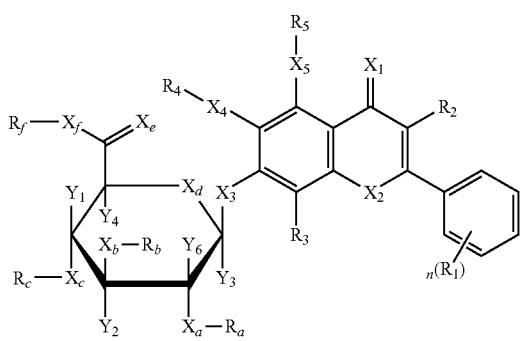

(I)

wherein

Each X1, X2, X3, X4, X5, Xa, Xb, Xc, Xd, Xe and Xf, independently, designate O or S;

Each Y1, Y2, Y3, Y4, Y6, independently, designates H or a (C1-C10)alkyl radical;

Each R4, R5, Ra, Rb and Rc, independently, designates H, a (C1-C10)alkyl radial optionally substituted with 1 to 5 Ry groups, or a (C1-C10)alkyl-O—(C1-C10)alkyl radial, with each (C1-C10)alkyl radical able to be substituted with 1 to 5 Ry groups;

Each Ry, independently, designates Rq or a —(C2-C10) alkenyl, —(C2-C10)alkynyl, —(C3-C10)cycloalkyl, —(C8-C14)bicycloalkyl, —(C8-C14)tricycloalkyl, —(C5-C10)cycloalkenyl, —(C8-C14)tricycloalkenyl, phenyl, naphthyl, —(C14)aryl radical, with each one able to be substituted with one or several Rz radicals;

Each R1 R2, R3, independently, designates H or Rq or a —(C2-C10)alkenyl, —(C2-C10)alkynyl, —(C3-C10) cycloalkyl, —(C8-C14)bicycloalkyl, —(C8-C14)tricy-cloalkyl, —(C5-C10)cycloalkenyl, —(C8-C14)tricy-cloalkenyl, phenyl, naphthyl, —(C14)aryl radical, with each one able to be substituted with one or several Rz radicals;

Rf is H, (C1-C12) alkyl optionally substituted with 1 to 5 Ry radicals, (C1-C12)alkyl-O—(C1-C12)alkyl, with each (C1-C12)alkyl radical able to be substituted with 1 to 5 Ry groups;

Each Rq, independently, is CN, OH, halogen, N3, NO2, N(Rz)2, =NRz, CH=NRz, NRzOH, ORz, CORz, C(O)Rz, O(CO)ORz, SRz, S(O)Rz or S(O)2Rz;

Each Rz, independently, is —(C1-C6)alkyl, —(C2-C6) alkenyl, —(C3-C8)cycloalkyl, —(C3-C8)cycloalk-enyl, phenyl, an heterocycle having 3 to 5 branches, CH(halo)2 or C(halo)3; and n is 0, 1, 2, 3, 4 or 5 as well as the salts thereof, the optical isomers thereof and/or the diastereoisomers thereof.

11. Composition according to claim 2, comprising Baicalin that satisfies the following general formula (II):

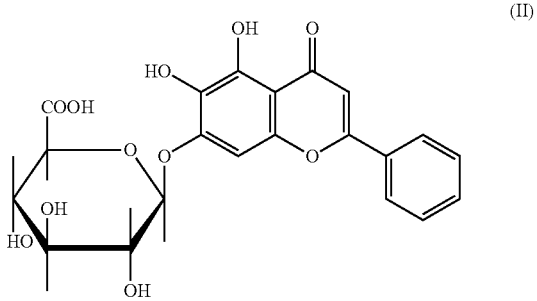

(II)

or a plant extract that contains it.

12. The composition according to claim 2, wherein said Baicalin and/or one of its derivatives or a plant extract containing it is present in concentrations of active substance ranging from 0.01% to 5% by weight with respect to the total weight of the composition.

13. The composition according to claim 3, wherein said Baicalin and/or one of its derivatives or a plant extract containing it is present in concentrations of active substance ranging from 0.01% to 5% by weight with respect to the total weight of the composition.

14. The composition according to claim 4, wherein said Baicalin and/or one of its derivatives or a plant extract containing it is present in concentrations of active substance ranging from 0.01% to 5% by weight with respect to the total weight of the composition.

15. The composition according to claim 2, wherein the superabsorbent polymer is chosen from among:
cross-linked sodium polyacrylates,
starches grafted by an acrylic polymer,
hydrolyzed starches grafted by an acrylic polymer,
polymers based on starch, gum and cellulose derivative, and mixtures thereof.

16. The composition according to claim 1, characterized in that it has a pH of 6.1 to 6.4.

17. A method of reducing pigmentation induced by UV rays comprising topically applying a composition defined in claim 1 to a subject in need thereof.

* * * * *